United States Patent
Burns et al.

(10) Patent No.: US 6,794,650 B2
(45) Date of Patent: Sep. 21, 2004

(54) METHOD AND APPARATUS FOR MONITORING SURFACE CONDITION OF A BOWLING LANE

(75) Inventors: Douglas S. Burns, Melbourne, FL (US); Alan J. Siegel, Melbourne, FL (US)

(73) Assignee: Ensco, Inc., Falls Church, VA (US)

( * ) Notice: Subject to any disclaimer, the term of this patent is extended or adjusted under 35 U.S.C. 154(b) by 130 days.

(21) Appl. No.: 10/141,784

(22) Filed: May 10, 2002

(65) Prior Publication Data

US 2002/0166971 A1 Nov. 14, 2002

Related U.S. Application Data

(60) Provisional application No. 60/289,810, filed on May 10, 2001.

(51) Int. Cl.[7] .............................. B05C 1/00; G01N 21/00
(52) U.S. Cl. ................................ 250/341.8; 250/339.11
(58) Field of Search ....................... 250/341.8, 339.11, 250/226, 559.4, 559.22, 559.27, 552; 356/51, 326, 328, 419

(56) References Cited

U.S. PATENT DOCUMENTS

| | | | |
|---|---|---|---|
| 3,619,072 A | 11/1971 | O'Hara et al. | |
| 3,892,485 A | 7/1975 | Merritt et al. | |
| 4,092,068 A * | 5/1978 | Lucas et al. | 356/73 |
| 4,464,050 A * | 8/1984 | Kato et al. | 356/239.1 |
| 4,570,069 A | 2/1986 | Gager | |
| 4,690,553 A * | 9/1987 | Fukamizu et al. | 356/51 |
| 4,692,620 A | 9/1987 | Rosenthal | |
| 4,755,054 A * | 7/1988 | Ferree | 356/418 |
| 4,800,279 A | 1/1989 | Hieftje et al. | |
| 4,982,601 A | 1/1991 | Troxell | |
| 5,145,785 A | 9/1992 | Maggard et al. | |
| 5,194,910 A | 3/1993 | Kirkpatrick, Jr. et al. | |
| 5,206,701 A | 4/1993 | Taylor et al. | |
| 5,218,206 A * | 6/1993 | Schmitt et al. | 250/339.11 |
| 5,517,427 A | 5/1996 | Joyce | |
| 5,548,393 A | 8/1996 | Nozawa et al. | |
| 5,717,220 A * | 2/1998 | Burkholder et al. | 250/559.22 |
| 5,786,915 A * | 7/1998 | Scobey | 398/82 |
| 5,935,333 A * | 8/1999 | Davis | 118/681 |
| 5,962,853 A * | 10/1999 | Huth-Fehre et al. | 250/339.11 |
| 6,049,387 A * | 4/2000 | Griesinger | 356/419 |
| 6,452,179 B1 | 9/2002 | Coates et al. | |
| 2002/0185604 A1 | 12/2002 | Coates et al. | |

\* cited by examiner

*Primary Examiner*—Constantine Hannaher
*Assistant Examiner*—Otilia Gabor
(74) *Attorney, Agent, or Firm*—Nixon Peabody LLP; Jeffrey L. Costellia

(57) ABSTRACT

A topical recognition apparatus for monitoring surface condition of a bowling lane surface and a method thereof. The apparatus has a lamp that provides light on the bowling lane surface, and a sensor positioned proximate to the bowling lane surface, the sensor being adapted to sense light provided by at least one lamp after the light is scattered off the bowling lane surface, the scattered light being indicative of a surface condition of the bowling lane. The surface condition of the bowling lane monitored may be the quantity of oil on the bowling lane surface and/or the amount of wear on the bowling lane surface.

35 Claims, 4 Drawing Sheets

METHOD AND APPARATUS FOR MONITORING SURFACE CONDITION OF A BOWLING LANE

This application claims priority to U.S. Provisional Application No. 60/289,810 filed May 10, 2001.

FIELD OF THE INVENTION

This invention relates generally to a method and apparatus for monitoring the surface condition of a bowling lane.

BACKGROUND OF THE INVENTION

An important aspect of the game of bowling is the surface condition of the bowling lane. One aspect of the lane condition relates to the amount and distribution of oil that is applied to the surface of the lane. Tournament play and competition requires that the lane surface be oiled with deference to very strict application standards in terms of the "number of units of oil" that may be applied to various areas of the lane surface since the oil affects how the bowling ball rolls down the bowling lane. In this regard, the lane surface can only have oil applied a certain distance down the lane. In addition, there are stringent requirements that govern the cross lane distribution of oil as well. Lanes are typically 39½ "boards" wide and tournament rules govern how oil may be applied across these boards.

In general, competitive bowlers such as professionals and serious amateurs, as well as bowling alley proprietors, do not have access to high quality information about the quantitative distribution of oil on a bowling lane surface. The subject continues to be a contentious matter between proprietors and patrons as part of an ongoing debate on how the chosen prescription for lane maintenance effects bowler's scores. Furthermore, the lack of hard data threatens the future of professional bowling and its elevation to an Olympic level sport.

Complicating the proper maintenance of lane condition is the fact that the lane dressing (i.e. oil) applied to the surface of a bowling lane migrates down and across the lane as bowling balls travel toward the pins. Known methods for measuring the amount of oil on a bowling lane involve the addition of ultra violet (UV) additives to the oil. These methods do not provide a direct measurement of the oil on the lane surface but instead, merely detect the concentration of dye or additive present in the oil. The potential adverse health effects which may occur from consistent and prolonged exposure to UV additives makes the use of such additives undesirable.

The first method for gathering information about oil on a lane surface is a process known as "taping". This method involves using a device to affix adhesive tape applying constant pressure across a lane surface, and lifting oil along with the UV additives with the tape for laboratory analysis. This method is indirect in that it measures the amount of additive present, and not the oil. In addition, this method is destructive in that it modifies the lane surface. This method also has other disadvantages in that it is often inaccurate, manually tedious, expensive, and entirely impractical for routine use. Due to these constraints, measurements are only taken at widely spaced intervals along the length of the lane, and therefore, information provided is largely discontinuous.

The second qualitative method as disclosed in U.S. Pat. No. 4,982,601 to Troxell, requires the addition of dyes or additives to lane conditioners that are selectively responsive to certain wavelengths in the electromagnetic spectrum. This method requires the strategic placement of special light sources along the length of the lane surface as well as cameras which may be equipped with optical filters. At best, this method provides a stronger visual return from areas characterized by higher concentrations of additive, and does not provide a direct and quantitative measurement of oil at any point on the surface of a lane.

Another aspect of bowling lane surface condition is surface wear and degradation. Areas of excessive wear or cracking on the bowling lane surface can cause the conditioner to seep into the underlying wood. Pinhole "leaks" in protective laminates such as Guardian™ may also occur. Once the bowling lane is damaged, repairs are generally very expensive. Presently, there are no known methods for effectively monitoring the wear and degradation of a bowling lane.

Therefore, there is an unfulfilled need for a method and apparatus for monitoring the surface characteristics of a bowling lane surface. In particular, there is an unfulfilled need for such a method and apparatus that can quantify the amount of oil on the lane surface of a bowling alley which avoids the limitations of the prior art. In addition, there is an unfulfilled need for a method and apparatus for monitoring wear of a bowling lane.

SUMMARY OF THE INVENTION

The primary object of the present invention is to provide a method and apparatus for monitoring the condition of the lane surface of a bowling alley.

One advantage of the present invention is that it provides a rapid, direct, nondestructive, and accurate method and apparatus for quantifying the amount of oil on a bowling lane surface.

Another advantage of the present invention is that it provides a method and apparatus to obtain a direct measurement of oil without requiring the addition of optically active dyes or additives.

Still another advantage of the present invention is that it provides a method and apparatus that uses near-infrared spectrophotometry to quantify oil on a variety of surfaces associated with the bowling lane, including, but not limited to, synthetic, Guardian®, and variety of woods such as pine, maple and others.

Yet another advantage of the present invention is that it provides a method for diagnosing the general condition of a lane surface by sensing areas of excessive wear or cracking where conditioner seepage to an underlying wood surface can occur.

A further advantage of one embodiment of the present invention is that it provides a novel apparatus for oil pattern topical recognition which is mounted on a bowling lane surface conditioning machine that scans the lane surface as the machine moves down the lane.

Yet another advantage of another embodiment of the present invention is that it provides a novel apparatus for oil pattern topical recognition which is built into the lane.

Another advantage of yet another embodiment of the present invention is that it provides a novel hand-held apparatus for oil pattern topical recognition.

These and other objects, features, and advantages of the present invention are attained by a topical recognition apparatus for monitoring surface condition of a bowling lane surface. The apparatus has at least one lamp that provides light which impinges on the bowling lane surface, and at least one sensor positioned proximate to the bowling lane surface. The sensor is adapted to detect light provided by the lamp after the light is scattered and/or reflected, hereinafter referred to as scattered, off the bowling lane surface, where the scattered light is indicative of the surface condition of the bowling lane. More specifically, the device and method in accordance with the present invention is based on diffuse reflectance where light penetrates the lane surface a certain distance depending on material properties. Light that excites the vibrational and rotational modes of the sample molecules is absorbed. The balance of the light is scattered in all directions and carries information about the lane surface, such as the amount of oil that is on or under the surface, the thickness of the protective layers, etc.

In one embodiment of the present invention, the topical recognition apparatus is adapted to be moved lengthwise along the bowling lane during operation. In addition, in other embodiments, the lamp and/or the sensor is traversed widthwise across the bowling lane during operation.

In accordance with another embodiment of the present invention, the apparatus includes a spectrophotometer which determines characteristics of light scattered off the bowling lane surface, and a processor that analyzes characteristics of the light scattered off the bowling lane surface to thereby determine surface condition of the bowling lane. The apparatus may also include a display that displays the determined surface condition of the bowling lane.

In another embodiment of the present invention, the lamp provides, visible, near infrared or infrared light to the bowling lane surface and the sensor is an optical probe that carries the signal to a spectrophotometer. Preferably, in accordance with another embodiment a plurality of lamps and a plurality of sensors positioned across the bowling lane are used. An optical multiplexer is provided in another embodiment for sequencing signals from the plurality of sensors, and a spectrophotometer which receives the sequenced signals from the optical multiplexer, determines characteristics of the light scattered off the bowling lane surface. The determined characteristics of the scattered light are analyzed by a processor to determine the surface condition of the bowling lane in the preferred embodiment, the results of which are depicted on a display.

The surface condition of the bowling lane monitored by the apparatus may be the quantity of oil on the bowling lane surface and/or the amount of wear on the bowling lane surface. The topical recognition apparatus may be mounted on a lane conditioning machine adapted to be moved lengthwise along the bowling lane, be integrated with the bowling lane, or be a small hand-held unit.

In accordance with another aspect of the present invention, a method for monitoring surface condition of a bowling lane is provided. Steps include providing light on the bowling lane surface so that the light is scattered off the bowling lane surface. The scattered light is indicative of the surface condition of the bowling lane. The method also includes the steps of sensing the scattered light off the bowling lane surface, and determining a surface condition of the bowling lane based on the sensed scattered light. The step of providing light on the bowling lane surface may be attained by at least one lamp which provides visible, near infrared, or infrared light, while the step of sensing the scattered light off the bowling lane surface is attained by at least one optical sensor. In such an embodiment, the method may also include the step of traversing the lamp and the sensor widthwise across the bowling lane.

In accordance with still another embodiment, the step of providing light on the bowling lane surface is attained by a plurality of lamps positioned across the bowling lane while the step of sensing the scattered light off the bowling lane surface is attained by a plurality of sensors positioned across the bowling lane. In another embodiment, the method further includes the step of sequencing signals from the plurality of sensors and the step of determining characteristics of the scattered light. Moreover, in another embodiment, the method further includes the step of analyzing the determined characteristics of the scattered light and the step of displaying the determined surface condition of the bowling lane surface. The above summarized method of the present invention may be used to determine the quantity of oil on the bowling lane surface and/or the amount of wear on the bowling lane surface.

These and other objects, features, and advantages will become more apparent from the following detailed description of the preferred embodiments of the present invention when viewed in conjunction with the accompanying drawings.

DESCRIPTION OF THE PREFERRED EMBODIMENTS

Figure 1:
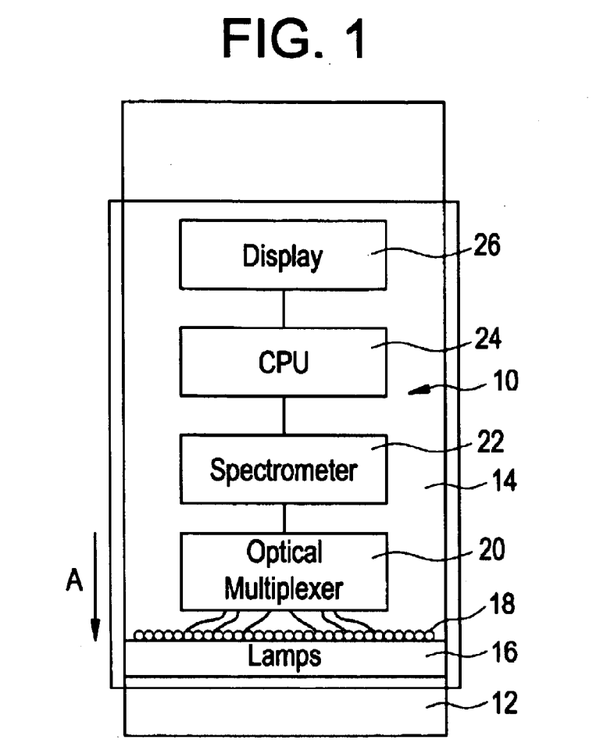
FIG. 1 is a schematic block diagram of a topical recognition apparatus for determining quantity of oil in accordance with one embodiment of the present invention which is mounted on a lane conditioning machine.

The method and apparatus of the present invention as described herein below allows monitoring of the condition of the lane surface of a bowling alley and may be used to monitor the quantity of oil on the bowling lane surface and/or the amount of wear on the bowling lane surface. FIG. 1 is a schematic block diagram of a topical recognition apparatus 10 for monitoring surface condition of a bowling lane in accordance with one embodiment of the present invention which is mounted on a lane conditioning machine 14. As shown, the topical recognition apparatus 10 is mounted on the lane conditioning machine 14 over the surface of a bowling lane 12 to allow its operation as the lane conditioning machine 14 is moved down the bowling lane 12, for instance, in the direction of the arrow "A" in FIG. 1. It should be noted that although the lane conditioning machine 14 is not described in detail, the lane conditioning machine 14 may be of the type that is pushed down the bowling lane 12 or in other embodiments, may be automated to go down the bowling lane 12 under user's control.

Figure 2:
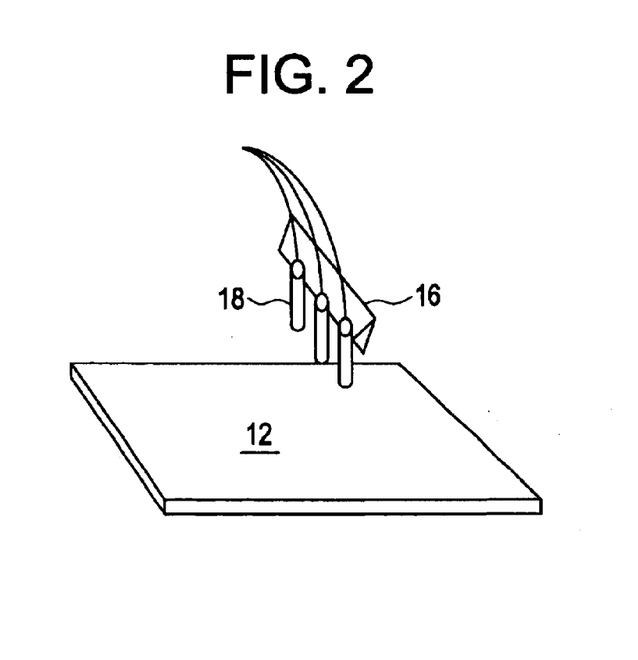
FIG. 2 is a partial schematic perspective view of the lamp and optical sensors of FIG. 1.

In the illustrated embodiment, at the front of the conditioning machine 14, a lamp 16 or a plurality of lamps are mounted to provide light across the width of the bowling lane 12. The lamp is followed by a line of optical probes or sensors 18 which are mounted to extend across the width of the bowling lane 12. FIG. 2 is a partial schematic perspective view of the lamp 16 and the sensors 18 of FIG. 1. As illustrated, the lamp 16 provides light onto the surface of the bowling lane 12, some of the light being absorbed and some of the light being scattered by the surface of the bowling lane 12. In accordance with the present invention, the sensors 18 sense the scattered light off the surface of the bowling lane 12, the scattered light carrying information about the lane surface which may be analyzed using a spectrophotometer or other device to monitor the surface condition of the bowling lane 12.

Referring again to FIG. 1, an optical multiplexer 20 sequences the output signals from the plurality of sensors 18 and sequentially provides the output signals to a spectrophotometer 22. The spectrophotometer 22 determines characteristics of light scattered off the surface of the bowling lane 12 and provides the information to a processor such as CPU 24. The CPU 24 provides the weighting factors described below to the data from the spectrophotometer 22, analyzes the signals, and displays the corresponding information regarding the condition of the bowling lane surface on display 26.

The above described topical recognition apparatus 10 may be used to directly determine the quantity of oil on the surface of the bowling lane 12 at any location on the lane without requiring the use of additives or dye in the oil, thereby avoiding the disadvantages and limitations of conventional measurement methods described previously.

The operation of the topical recognition apparatus 10 is based on diffuse reflectance where the light provided by lamp 16 penetrates the surface of the bowling lane 12 a certain distance depending on material properties of the oil and the surface. A portion of the light provided by the lamp 16 is absorbed by the oil and lane material itself, the depth of penetration being a function of lamp intensity and material properties. The balance of the light is scattered off the surface of the bowling lane 12 in all directions, the scattered light carrying information about the lane surface. For instance, the scattered light carries information about the amount of oil that is on the surface of the bowling lane 12, as well as other information as discussed below. There is a dramatic and significant difference in the spectra returned based on surface type and with increasing or decreasing quantities of lane oil. Spectral data is correlated to the amount of oil on the surface for each type of lane surface including, but not limited to, synthetic, Guardian®, and variety of woods such as pine, maple and others. Of course, in other embodiments of the present invention, an optical probe may also be provided that carries the optical signal to a spectrophotometer that picks up and analyzes the scattered light.

The evaluation of the amount of oil on the bowling lane surface is made by providing and detecting visible, near infrared, and/or infrared wavelengths that are in the range of 400–2500 nanometers (nm) using the lamp 16 and sensors 18. More specifically, the lamp 16 provides white light having components at various wavelengths of which may include, visible, near infrared, and/or infrared wavelengths. In this regard, it should be understood that the term "optical" as used herein does not specifically refer to the wavelengths of light that are visible but also includes all wavelengths of light including the above noted near infrared and infrared wavelengths.

The sensors 18 are adapted to sense the wavelengths of scattered light off the surface of the bowling lane 12 that is of interest, the scattered light carrying information about the lane surface as previously described. For instance, for the 400–1100 nm wavelengths, silicon detectors may be used as sensors 18 whereas for the 1100–2500 nm wavelengths, PBS detectors may be used. Alternatively, for wavelengths upto 1700 nm, InGaAs detectors could be used. Of course, other detectors may also be used in other embodiments of the present invention as well. Moreover, as also previously noted, optical probes may also alternatively be used to gather and carry the scattered light to a spectrophotometer that includes such detectors that are specific to different regions of the light wavelength.

A training set of calibration samples is initially evaluated in order to determine the wavelength or wavelengths that optimally correlate to the amount of oil on the bowling lane 12. The training set of calibration samples is also evaluated to determine the optimum values of the weighting factors, i.e., the importance of each wavelength, at each of the determined wavelength(s). These evaluations can be accomplished through the use of a statistical methods and algorithms that allows the quantity of oil on or below (within the depth of light penetration) the surface to be predicted, and stored in a memory device (not shown) accessible by the CPU 24 during analysis to accurately determine the amount of oil on the surface of the bowling lane 12 during actual use. Of course, wavelength regions with the maximum weighting coefficients varies depending on the surface and the type of oil. For example, lane surfaces with Guardian® protective laminates have wavelength regions with the maximum weighting coefficients include, but are not limited to, 1600–1850 nm, 1950–2050 nm and 2200–2350 nm. In the case of certain synthetic lane surfaces such as Headen® 620, these and other wavelengths such as 800–1200 nm can be correlated to oil on the lane surface.

In addition, the scattered light also carries information about the amount of oil that is under the surface of the lane as well as the thickness of the protective layers, etc. Thus, the above noted method also enables the determination of quantity of oil below the surface of the protective layers within the depth of light penetration as well as the determination of the wavelength(s) and weighting factors that correspond to the thickness of protective layers. Therefore, there may be a number of wavelengths that are used to monitor and/or predict multiple properties such as the amount of oil and the thickness of the protective layer, thus making the method of the present invention multivariate.

In such an embodiment as shown where the topical recognition apparatus is mounted to the lane conditioning machine 14, the lane conditioning machine 14 may then be used to apply oil based on the amount of oil found on the surface of the bowling lane 12 as determined by the topical recognition apparatus 10. In this regard, the topical recognition apparatus may be mounted on either the front and/or back of the lane conditioning machine 14. In addition, the topical recognition apparatus 10 may also be adapted to control the operation of the alley conditioning machine 14 in response to lane surface oil data received and analyzed.

The above described topical recognition apparatus 10 may also be used to monitor the amount of wear on the surface of the bowling lane 12. In particular, the topical recognition apparatus 10 may be used to diagnose the general condition of a bowling lane surface by sensing areas of excessive wear or cracking where conditioner seepage to an underlying, more vulnerable wood surface can occur. Pinhole "leaks" in protective laminates such as Guardian™ may also be detected in a likewise manner. In addition, the degradation, or gradual wearing away, of the Guardian™ may be monitored with the topical recognition apparatus 10 of the present invention. This, again, may be attained in the manner previously described with respect to determining the amount of oil that is present on and/or below the surface of the bowling lane 12. Of course, a training set of calibration samples may be used in a manner described above to determine empirical correlation between the sensed scattered light and the amount of wear and/or degradation of the bowling lane 12, the details of which are omitted here to avoid repetition.

Figure 3A:
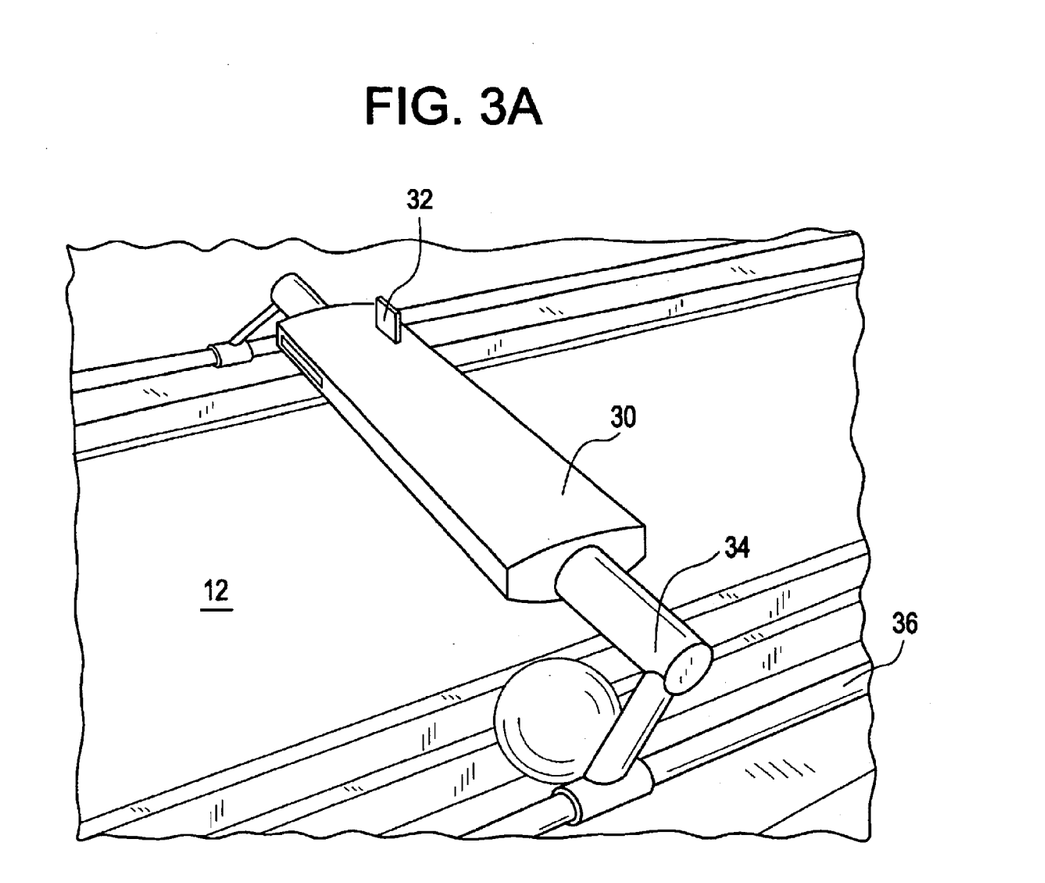
FIG. 3A is a perspective view of a topical recognition apparatus for determining quantity of oil in accordance with another embodiment of the present invention which is incorporated into the lane of the bowling ally.
Figure 3B:
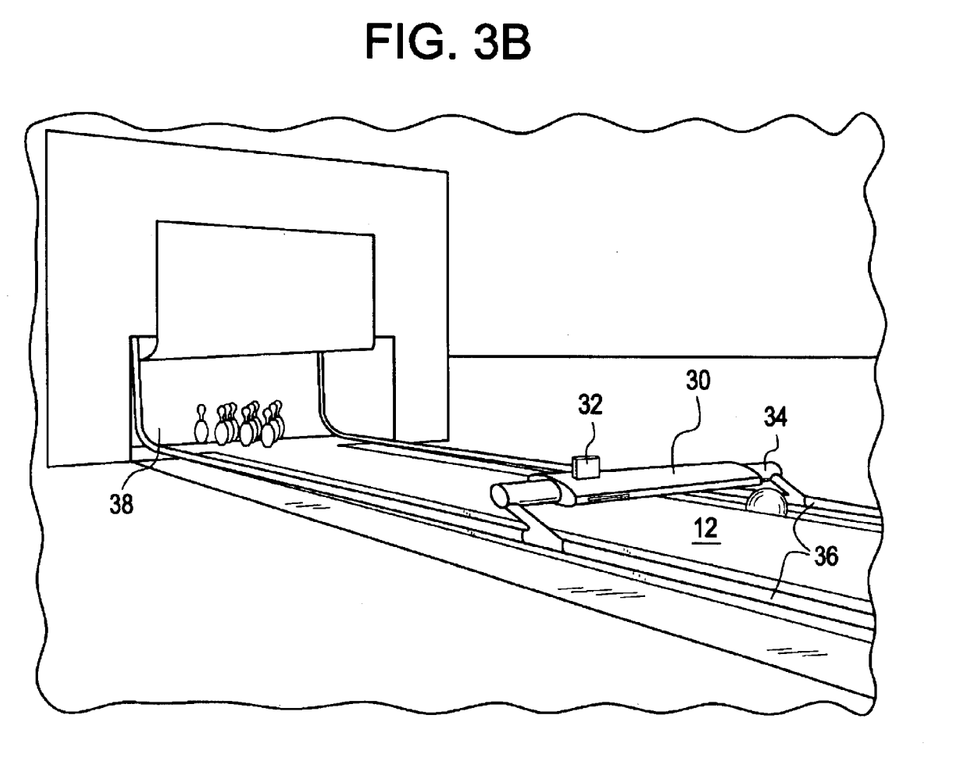
FIG. 3B is another enlarged perspective view of the topical recognition apparatus shown in FIG. 3A.

FIGS. 3A and 3B each show perspective views of another embodiment of the present invention. The topical recognition apparatus 30 is similar to that described in FIGS. 1 and 2 and may be used to monitor quantity of oil on the surface of the bowling lane 12 and/or to monitor the wear and degradation of the surface of the bowling lane 12. As can be appreciated, in this embodiment, the topical recognition apparatus 30 is built into the bowling lane 12 so that it can travel the length of the bowling lane 12 while measuring the amount of oil and the wear throughout the surface of the bowling lane 12. In this regard, the apparatus 30 is mounted to a cross member 34 which is movably supported on rails 36 positioned along the gutters of the bowling lane 12. When not in use, the topical recognition apparatus 30 is moved out of the lane 12, for instance, into the pin reset area via the upwardly extending rails 38.

As previously described relative to FIGS. 1 and 2, a plurality of lamps (not shown) of the topical recognition apparatus 30 are mounted to provide light across the width of the bowling lane 12 while the plurality of sensors (not shown) is provided to sense the scattered light off the surface of the bowling lane 12. Again, the scattered light carries information about the condition of the surface of the bowling lane 12. As also previously described, an optical multiplexer, spectrophotometer, and CPU (not shown) are preferably provided so that the output of the plurality of sensors may be analyzed and displayed on display 32.

Figure 4:
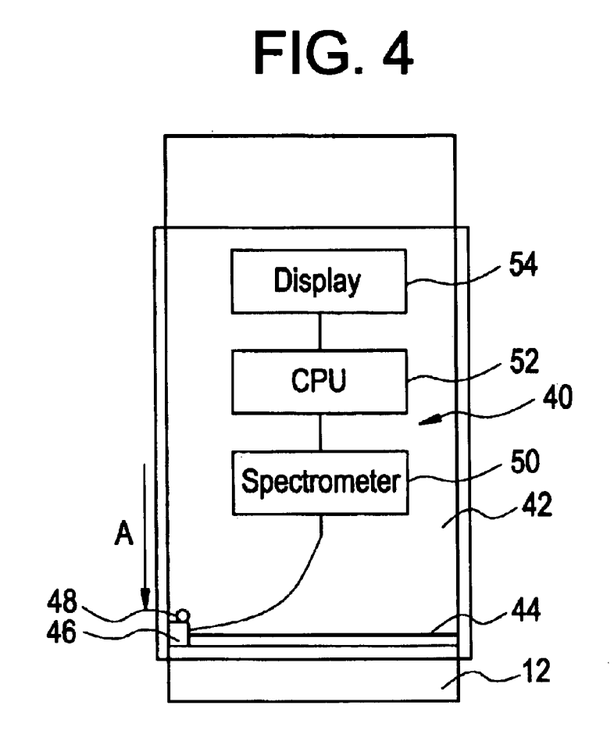
FIG. 4 is a schematic block diagram of a topical recognition apparatus for determining quantity of oil in accordance with another embodiment of the present invention in which the lamp and sensor are traversed widthwise across the bowling lane.

In the above described embodiments of FIGS. 1 to 3B, the topical recognition apparatus was provided with a plurality of lamps and a plurality of sensors positioned across the width of the bowling lane. However, in other embodiments, a single optical sensor and/or a single lamp may be used to minimize cost and electronic complexity of the topical recognition apparatus 40. In this regard, FIG. 4 shows a schematic block diagram of a topical recognition apparatus 40 for monitoring surface conditions of a bowling lane 12 that is also mounted to an alley conditioning machine 42 similar to that of embodiment shown in FIG. 1. Again, the monitored surface condition may be the quantity of oil and/or the wear and degradation of the surface of the bowling lane 12. In this embodiment of the present invention, the surface of the bowling lane 12 is scanned by traversing the lamp 46 and sensor 48 widthwise across the bowling lane via a drive mechanism having a guide rod 44. The output of the sensor 48 may then be provided to the spectrophotometer 50 for analysis by CPU 52 and displayed on display 54, an optical multiplexer not being necessary since only one sensor is provided in the present embodiment. In this manner, a single lamp 46 and/or sensor 48 may be used instead of the plurality of lamps and/or sensors as in the previously described embodiments thereby minimizing cost and complexity of the topical recognition apparatus 40. The lamp 46 and sensor 48 are also moved along the length of the bowling lane 12 with the alley conditioning machine 42. Of course, it should be evident to one of ordinary skill in the art based on the teachings herein that in other embodiments, multiple lamps and/or sensors may be used which only partially extend across the width of the bowling lane 12. This will allow more rapid gathering of required lane surface data and yet, reduce cost and complexity as compared to the embodiment of FIGS. 1 and 2.

Figure 5:
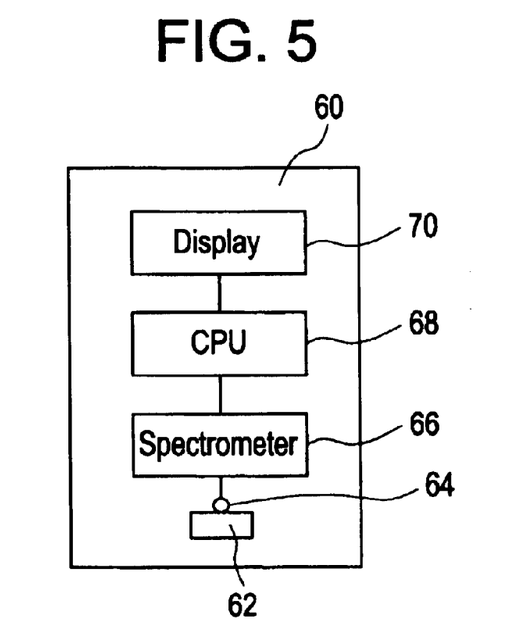
FIG. 5 is a schematic block diagram of a topical recognition apparatus for determining quantity of oil in accordance with one embodiment of the present invention which is sized as a hand-held unit.

FIG. 5 is a schematic block diagram of a topical recognition apparatus 60 for monitoring surface condition of the surface of a bowling lane such as the amount of oil and/or wear in accordance with yet another embodiment of the present invention which is sized as a hand-held unit. This hand-held unit can be placed at any distance down a bowling lane from the foul line to scan the cross-lane pattern at the particular distance down the bowling lane. As can be seen, the topical recognition apparatus 60 includes a lamp 62 for providing a light to the surface of the bowling lane and sensor 64 for sensing the scattered light in a manner previously described. The output of the sensor 64 is provided to the spectrophotometer 66 for analysis by CPU 68 and the results are displayed on display 70 in the manner previously described.

The above described embodiments of the present invention may be applied according to the requirements of the specific application. For example, to control the application of oil to the lane, a topical recognition apparatus may be built into a lane conditioning machine as described relative to the embodiment of FIG. 1. The desired density of data obtained over the bowling lane surface may also serve as a guide to which embodiment is most suitable for the given application. For instance, for a more detailed analysis such as for monitoring surface conditions of every board of the bowling lane at numerous distances down the bowling lane, the topical recognition apparatus may be built into the bowling lane in the manner described relative to the embodiment of FIGS. 3A and 3B. Such an embodiment is especially advantageous for monitoring the surface condition of the bowling lane various times throughout a series of games, such as during a tournament.

If the amount of time required for determining the conditions of the bowling lane surface is not important, the embodiment of FIG. 4 may be used which will reduce complexity and cost of the topical recognition apparatus. Of course, the embodiments described above may also be used merely to scan few locations of the bowling lane such as either across the lane or at various distances from the foul line if a rapid scan is needed for a less detailed analysis of the lane condition. This application may be particularly relevant in competitive environments such as in televised tournament play where there is a limited amount of time to scan the surface of the bowling lane. Of course, if time permits, a more detailed map may be generated of the surface by scanning in more locations of the bowling lane.

Finally, a simpler, less expensive design such as the hand-held device as described in the embodiment of FIG. 5 could be used for rapid spot analyses. In such application requirements, the hand-held device can be used to obtain the cross lane oil distribution at individual distances from the foul line of the bowling lane. The device would be manually placed across the lane at selected distances down the lane, and oil at any number of distances can be measured. Of course, the above only describes some of the considerations taken into account in determining which embodiment of the topical recognition apparatus in accordance with the present invention should be used in a particular application, and other considerations may be taken into account as well.

Lastly, it should also be noted that the present method and apparatus, for instance, the hand held unit of FIG. 5 may also be used to assess the condition of bowling balls. Generally, bowling balls are made from a variety of rubber, plastic, urethane, and reactive resin compounds. For the bowling ball to react to the bowling lane surface, the ball's surface should contact the bowling lane surface in a manner that allows the ball to respond as designed. However, with use, many bowling balls eventually become saturated with oil in the ball's track area and eventually lose their effectiveness to respond under conditions for which they were designed. In such cases, the bowling ball must be baked to purge the oil and restore it to something close to original efficiency. Currently, the bowing shop professional has no quantitative method for determining the content of absorbed oil in the track area of the bowling ball. The above described method and apparatus of the present invention can thus, be readily used for such determination.

While various embodiments in accordance with the present invention have been shown and described, it is understood that the invention is not limited thereto. The present invention may be changed, modified, and further applied by those skilled in the art. Therefore, this invention is not limited to the detail shown and described previously, but also includes all such changes and modifications.

We claim:

1. A topical recognition apparatus for monitoring a surface condition of a bowling lane surface, the apparatus comprising:
    at least one lamp that provides light on said bowling lane surface; and
    at least one sensor positioned proximate to said bowling lane surface, said at least one sensor being adapted to sense light provided by said at least one lamp after said light is scattered off said bowling lane surface, said scattered light being indicative of said surface condition of said bowling lane;
    wherein said surface condition of said bowling lane monitored by said apparatus is quantity of oil on said bowling lane surface.

2. The apparatus of claim 1, wherein said topical recognition apparatus is adapted to be moved lengthwise along said bowling lane during operation.

3. The apparatus of claim 1, wherein said at least one lamp is traversed widthwise across said bowling lane during operation.

4. The apparatus of claim 1, wherein said at least one sensor is traversed widthwise across said bowling lane during operation.

5. The apparatus of claim 1, further comprising a spectrophotometer which determines characteristics of light scattered off said bowling lane surface.

6. The apparatus of claim 1, further comprising a processor that analyzes characteristics of said light scattered off said bowling lane surface to determine said surface condition of said bowling lane.

7. The apparatus of claim 1, further comprising a display that displays said determined surface condition of said bowling lane.

8. The apparatus of claim 1, wherein said at least one lamp provides at least one of visible, near infrared, and infrared light to said bowling lane surface.

9. The apparatus of claim 8, wherein said at least one sensor is at least one optical sensor adapted to detect at least one of visible, near infrared, and infrared light.

10. The apparatus of claim 1, wherein said at least one sensor is a plurality of sensors positioned across said bowling lane.

11. The apparatus of claim 10, wherein said at least one lamp is a plurality of lamps positioned across said bowling lane.

12. The apparatus of claim 10, further comprising an optical multiplexer for sequencing signals from said plurality of sensors.

13. The apparatus of claim 12, further comprising a spectrophotometer which receives said sequenced signals from said optical multiplexer, and determines characteristics of said light scattered off said bowling lane surface.

14. The apparatus of claim 13, further comprising a processor that analyzes said determined characteristics of said scattered light to determine said surface condition of said bowling lane.

15. The apparatus of claim 14, further comprising a display that displays said determined surface condition of said bowling lane.

16. The apparatus of claim 10, wherein said plurality of sensors are adapted to sense different wavelengths.

17. The apparatus of claim 16, wherein said at least one lamp is a plurality of lamps that provides light of at least two different wavelength ranges to said bowling lane surface.

18. The apparatus of claim 1, wherein said topical recognition apparatus is mounted on a lane conditioning machine adapted to be moved lengthwise along said bowling lane, and to at least apply oil on to said bowling lane surface.

19. A method for monitoring a surface condition of a bowling lane surface comprising the steps of:
    providing light on said bowling lane surface so that said light is scattered off said bowling lane surface, said scattered light being indicative of said surface condition of said bowling lane;
    sensing said scattered light off said bowling lane surface; and
    determining said surface condition of said bowling lane surface based on said sensed scattered light;
    wherein said surface condition of said bowline lane monitored is quantity of oil on said bowling lane surface.

20. The method of claim 19, wherein said step of providing light on said bowling lane surface is attained by at least one lamp.

21. The method of claim 20, wherein said light is at least one of visible, near infrared, and infrared light.

22. The method of claim 20, further including the step of traversing said at least one lamp widthwise across said bowling lane.

23. The method of claim 19, wherein said step of sensing said scattered light off said bowling lane surface is attained by at least one sensor.

24. The method of claim 23, wherein said at least one sensor is at least one optical sensor adapted to detect at least one of visible, near infrared, and infrared light.

25. The method of claim 23, further including the step of traversing said at least one sensor widthwise across said bowling lane.

26. The method of claim 19, wherein said step of sensing said scattered light off said bowling lane surface is attained by a plurality of sensors positioned across said bowling lane.

27. The method of claim 26, wherein said step of providing light on said bowling lane surface is attained by a plurality of lamps positioned across said bowling lane.

28. The method of claim 26, further comprising the step of sequencing signals from said plurality of sensors.

29. The method of claim 26, further comprising the step of determining characteristics of said scattered light.

30. The method of claim 29, further comprising the step of analyzing said determined characteristics of said scattered light.

31. The method of claim 30, further comprising the step of displaying said determined surface condition of said bowling lane surface.

32. The method of claim 26, wherein said plurality of sensors are adapted to sense different wavelengths.

33. The method of claim 32, wherein said step of providing light on said bowling lane surface is attained by a plurality of lamps that provide light of at least two different wavelength ranges to said bowling lane surface.

34. A topical recognition apparatus for monitoring a surface condition of a bowling lane surface, the apparatus comprising:

at least one lamp that provides light on said bowling lane surface;

at least one sensor positioned proximate to said bowling lane surface, said at least one sensor being adapted to sense light provided by said at least one lamp after said light is scattered off said bowling lane surface, said scattered light being indicative of said surface condition of said bowling lane; and a processor that analyzes characteristics of said light scattered off said bowling lane surface to determine said surface condition of said bowling lane;

wherein said surface condition of said bowling lane monitored by said apparatus is amount of wear on said bowling lane surface.

35. A method for monitoring a surface condition of a bowling lane surface comprising the steps of:

providing light on said bowling lane surface so that said light is scattered off said bowling lane surface, said scattered light being indicative of said surface condition of said bowling lane;

sensing said scattered light off said bowling lane surface; and determining said surface condition of said bowling lane surface based on said sensed scattered light;

wherein said surface condition of said bowling lane monitored is amount of wear on said bowling lane surface.

* * * * *